United States Patent [19]

Ooshiro et al.

[11] Patent Number: 4,537,073
[45] Date of Patent: Aug. 27, 1985

[54] INSPECTION METHOD OF SQUARE BILLET USING ELECTRONIC SCANNING

[75] Inventors: Takehiko Ooshiro, Kobe; Masayoshi Iwasaki, Hyogo; Kousuke Sahara, Kobe; Norio Suzuki, Kobe; Hitoshi Utsumi, Kobe; Kazuo Miyake, Kobe; Kenji Aburatani, Kobe, all of Japan

[73] Assignee: Kabushiki Kaisha Kobe Seiko Sho, Kobe, Japan

[21] Appl. No.: 563,953

[22] Filed: Dec. 21, 1983

[30] Foreign Application Priority Data

Dec. 24, 1982 [JP] Japan ................................ 57-233944
Feb. 14, 1983 [JP] Japan ................................ 58-23527

[51] Int. Cl.³ ............................................ G01N 29/04
[52] U.S. Cl. ........................................ 73/602; 73/641
[58] Field of Search ................. 73/626, 625, 602, 639, 73/641

[56] References Cited

U.S. PATENT DOCUMENTS

| 3,960,005 | 6/1976 | Vezina | 73/625 |
| 4,058,003 | 11/1977 | Macovski | 73/626 |
| 4,078,435 | 3/1978 | Kossoff et al. | 73/626 |
| 4,149,420 | 4/1979 | Hutchinson et al. | 73/626 |
| 4,332,171 | 6/1982 | Iida et al. | 73/626 |
| 4,344,327 | 8/1982 | Toshikawa et al. | 73/626 |
| 4,458,534 | 7/1984 | Kising | 73/625 |
| 4,472,973 | 9/1984 | Sugai et al. | 73/626 |

Primary Examiner—Anthony V. Ciarlante
Attorney, Agent, or Firm—Oblon, Fisher, Spivak, McClelland & Maier

[57] ABSTRACT

For the inspection of a square billet, an ultrasonic testing technique using an angle beam is performed using a phased array system. The phased array probe is disposed in a plane perpendicular to the axial direction of a square billet, at a prescribed distance from the surface of the billet and set at a prescribed angle with respect to the billet surface. The billet is inspected both inside and at the surface layer when the ultrasonic beam is electronically scanned. Inspection of the surface layer only is also performed using a surface defect inspection apparatus. Determination of internal defects (including subsurface defects) is performed based on the subtraction of information from the surface defect inspection from the information from the ultrasonic inspection.

4 Claims, 29 Drawing Figures

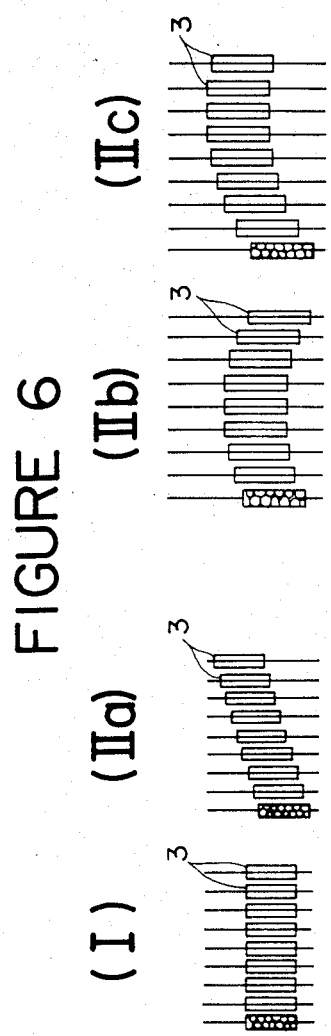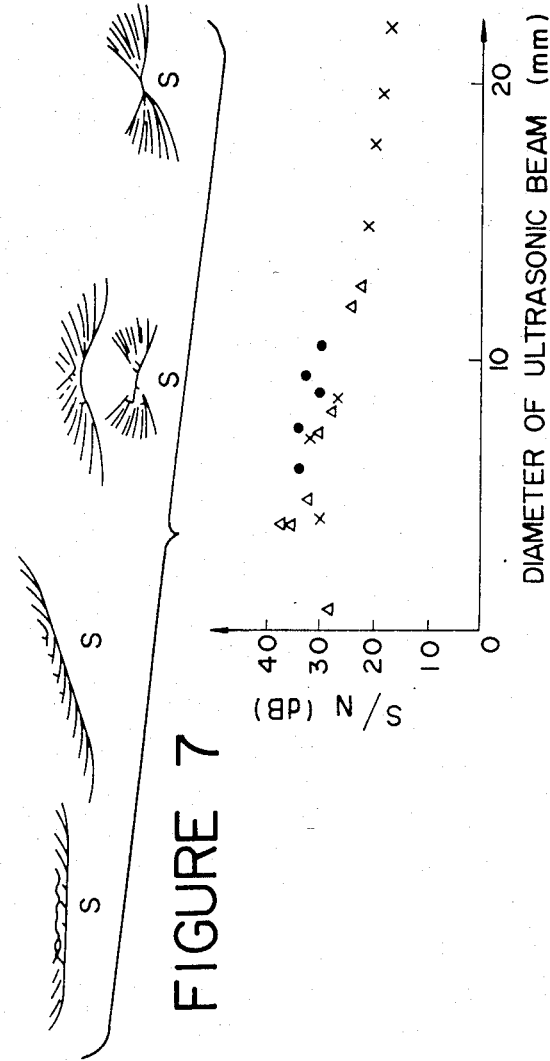

(a) (b) (c)

(a) (b) (c)

FIGURE 18
(a)   (b)    FIGURE 19
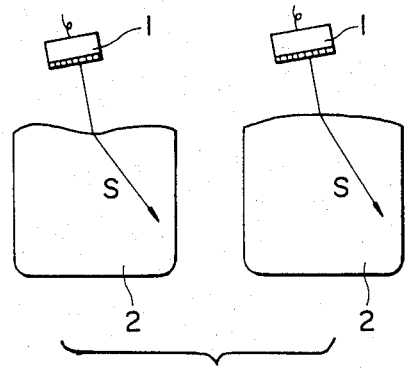 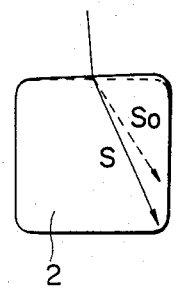
FIGURE 20
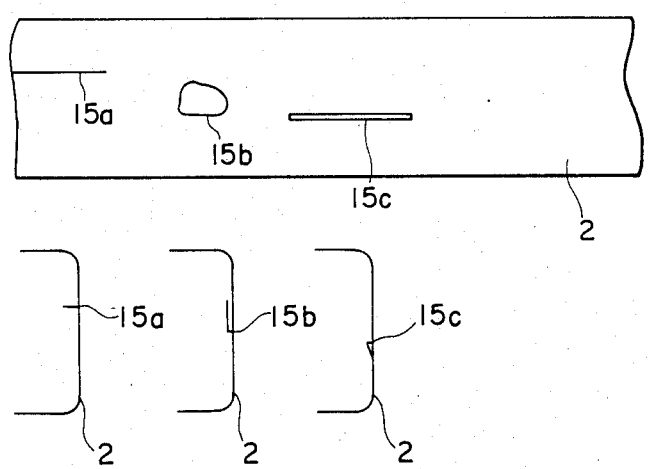

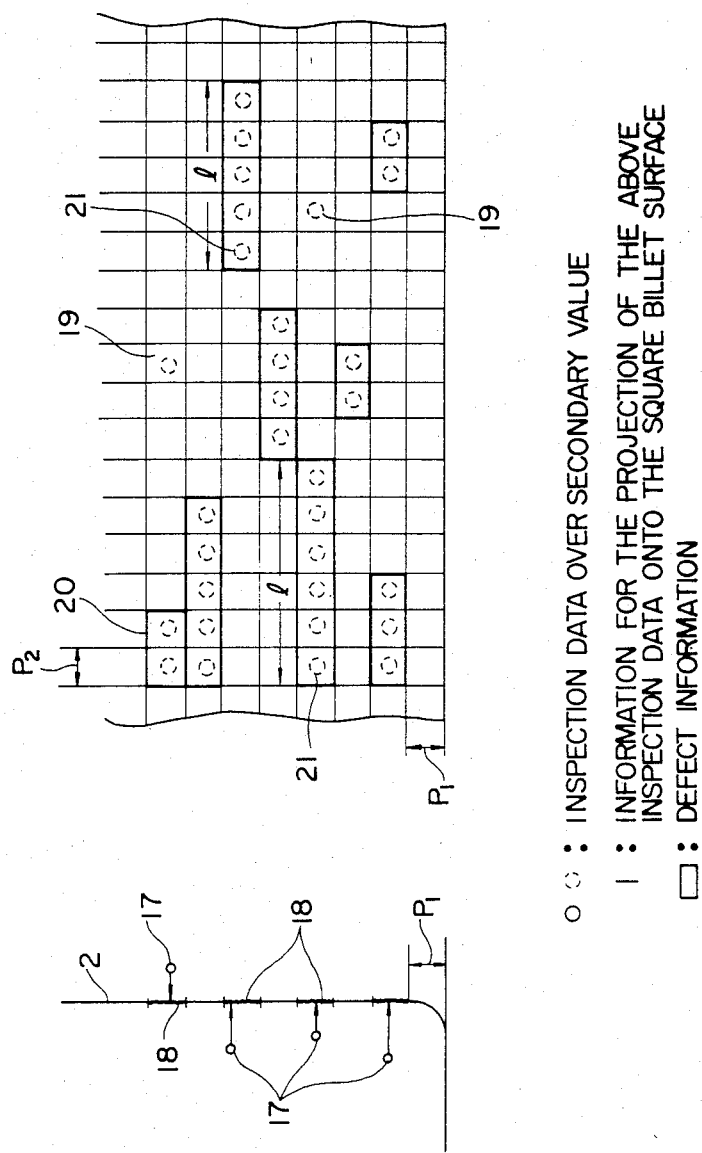

INSPECTION METHOD OF SQUARE BILLET USING ELECTRONIC SCANNING

BACKGROUND TO THE INVENTION

1. Field of the Invention

The present invention relates generally to an ultrasonic inspection method of a square billet and more particularly to an inspection method for effectively detecting internal defects including subsurface defects of the square billet throughout the inside and the entire surface layer (to a depth or several tens mm) in an on-line system and with high speed.

2. Description of the Prior Art

In the secondary conditioning industry of wire rod and steel bar processes have been implemented recently within the intention of saving labor and energy and reducing costs. As a result, the forming conditions of wire rod and steel bar became more difficult. Therefore cracking of work during cold forgoing and breakage during wire expanding caused by the inclusion of small foreign substances have become problems. In order to solve such problems, smelting techniques have been established which remove unwanted material outside of the furnace and prevent it from entering during pig iron manufacture and steel manufacture. This technique together with inspection techniques to detect the existence of small inclusions of foreign material has become essential from the viewpoint of quality assurance.

In regard to inspection techniques, ultrasonic inspection methods of a steel bar product are known where the steel bar is rotated or a probe is rotated around the steel bar and a focused ultrasonic beam enters the specimen. Similar inspection methods cannot be applied to a wire rod product on account of the small diameter, and inspection of the coiled final product throughout its whole circumference and length is impossible at the present time.

Inclusion of foreign matter in wire rod and steel bar, which causes problems, is present already in the raw material stage. Therefore, if inclusion is detected in the step of forming a square billet, the inside quality of the product can be assured. Particularly in the case of wire rod, ultrasonic inspection of the inside of a square billet may be utilized as a substitute for internal inspection of the product. Introduction of inside inspection techniques at an intermediate stop in the process permits a defective billet to be removed earlier. On account of the small length of the specimen and good inspection efficiency compared to inspection of the final product, inspection at an intermediate step has excellent efficiency. On the other hand high detecting accuracy is required even to detect small inclusions in order to assure reliability.

One ultrasonic inspection method of a square billet known in the part art, is the normal beam technique using a double crystal probe. In this method, a defect inside of a square billet can be detected but a subsurface defect cannot be detected. A subsurface defect is one just below the surface of the specimen. While technically a part of the interior rather than the surface, the fact that it lies just below the surface makes it difficult to detect by some methods. It is sometimes considered a separate type of defect from other internal defects because of this detection problem. When a square billet is machined into a product, an inclusion which causes the work to crack or the like exists frequently at the subsurface layer. Therefore the establishment of inspection methods for detecting internal defects including subsurface defects is required. Ultrasonic inspection methods of a square billet using mechanical scanning are also known. These methods are not suitable for high-speed manufacture which needs high-speed movement of the probe.

SUMMARY OF THE INVENTION

In view of above-mentioned problems in the prior art, one object of the present invention is to provide an ultrasonic inspection method of a square billet wherein internal defects including subsurface defects in the square billet can be effectively detected.

Another object of the invention is to provide an ultrasonic inspection method of a square billet wherein the existence of a defect can be detected accurately at the stage of a square billet.

Another object of the invention is to provide an ultrasonic inspection method of a square billet wherein electronic linear scanning or electronic sector scanning or a combination of electronic sector scanning and linear scanning is used.

Another object of the invention is to provide an ultrasonic inspection method of a square billet wherein internal defects or subsurface defects can be discriminated from surface defects by subtraction of information according to the inspection.

Another object of the invention is to provide an ultrasonic inspection method of a square billet wherein the square billet can be inspected throughout the inside and the entire surface in an on-line system and with high speed.

BRIEF DESCRIPTION OF THE DRAWINGS

A more complete appreciation of the invention and many of the attendant advantages thereof will be readily obtained as the same becomes better understood by reference to the following detailed description when considered if connection with the accompanying drawings, wherein:

FIGS. 6, (I) (IIa) (IIb) and (IIc) is a diagram illustrating the control mode of an ultrasonic beam by the phased array probe;

FIG. 7 is a graph illustrating the S/N ratio of a φ 2 mm side cave as a function of the ultrasonic beam diameter during an inspection of a square billet;

FIGS. 18 (a) and (b) is a diagram illustrating the incident point of an ultrasonic beam;

FIG. 19 is a diagram illustrating the determination of the incident point from a corner echo of a specimen;

FIG. 20 is a diagram illustrating types of surface defects;

FIGS. 22a and 22b are diagrams illustrating a collection of detected defects and information originated from one defect;

DETAILED DESCRIPTION OF THE INVENTION

The inspection method as an embodiment of the present invention will now be described in detail.

First, the introduction of angle beam inspection in the invention will be explained.

Figure 1:
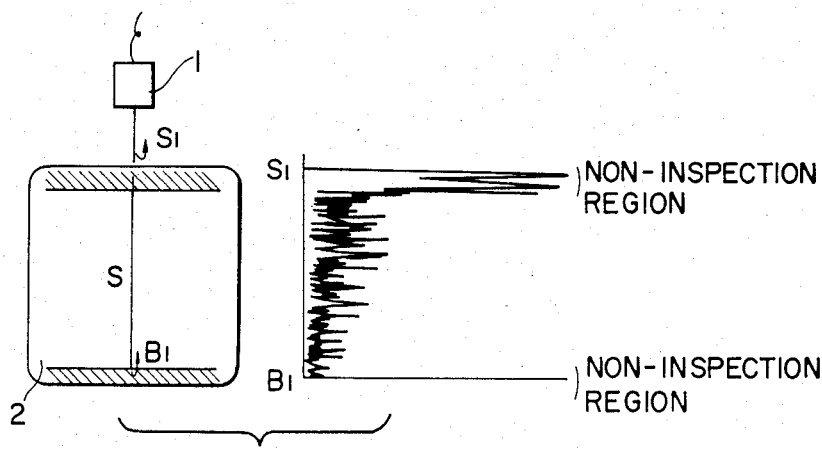
FIG. 1 is a view illustrating the dead zone of the normal beam technique of the prior art.
Figure 2:
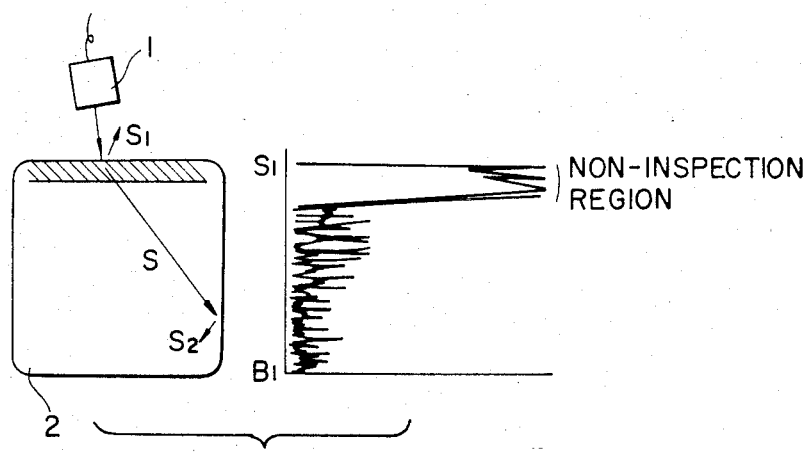
FIG. 2 is view illustrating the dead zone of an angle beam inspection according to the present invention.

In order to inspect internal defects of a square billet, the normal beam technique has been conventionally applied as above described. However, as clearly seen from FIG. 1, this method has disadvantages in that ultrasonic wave S which is transmitted from a probe 1 to a square billet 2 produce a reflection echo $S_1$ at the incident surface and a reflection echo $B_1$ at the bottom surface, whereby the region near the surface becomes a dead zone. On the contrary, when angle beam inspection is used as shown in FIG. 2, the reflection echo $S_1$ of ultrasonic wave S from the incident surface remains appreciable but the reflection echo $S_2$ from the lateral surface of the square billet 2 is directed downwards. Therefore, a dead zone based on this reflection does not occur at the lateral surface. If angle beam inspection is used and the lateral surface adjacent to the incident surface is made the inspection region, the inspection of the square billet 2 from the surface to inside is possible without a dead zone. A basic principle of the present invention is to inspect the inside of a square billet and the laterial surface layer adjacent to the incident surface using angle beam inspection tehcniques.

Next, the use of longitudinal waves in ultrasonic wave inspection techniques and especially in angle beam inspection will be explained.

Figure 3:
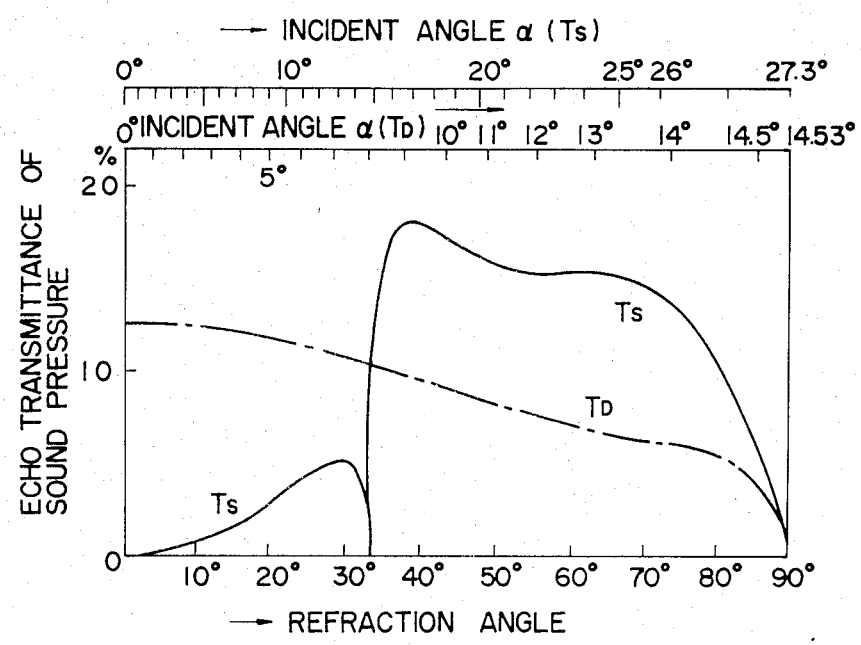
FIG. 3 is a graph illustrating the variation of the echo transmittance of sound pressure of longitudinal waves and transverse waves as a function of the incident angle and refraction angle.

The reason for using longitudinal waves is as follows: When transverse waves are used in an angle beam inspection as clearly seen from FIG. 3 disadvantages occur in that (1) the echo transmittance of sound pressure is small at refraction angles less than 34°, (2) the echo transmittance of second pressure varies sharply depending on the shape of the incident surface and a small error in setting in the incident angle when the inspection is effected at a refraction angle ranging from 30° to 40°, and (3) if a refraction angle ranging from 50° to 65° and having little variation in the echo transmittance of second pressure is used, the region below the lateral surface adjacent to the incident surface cannot be inspected geometrically. On the contrary, when longitudinal waves are used the variation in the echo transmittance of second pressure depending on the refraction angle is relatively small and continuous. Thus longitudinal waves are utilized in view of these advantages.

Figure 4:
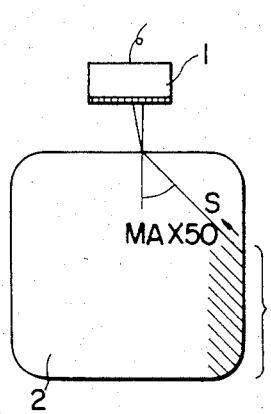
FIG. 4 is a view illustrating the inspection region in an angle beam inspection using longitudinal waves according to the invention.

The effective inspection region in sector scanning using angle beam inspection with longitudinal waves will be explained. Since large refraction angle transverse waves will also be induced in the square billet at fairly high levels (refer to FIG. 3) and the S/N ratio near the lateral surface decreases by receiving the lateral surface reflection echo, the refraction angle is limited to about 50° at most. That is, the inspection region is limited to the lower half of the lateral surface of the square billet 2 as shown in FIG. 4.

As described above, an ultrasonic beam must be scanned at high speed in order to inspect a square billet throughout its overall length using angle beam inspection. In this case, scanning systems are classified into mechanical scanning and electronic scanning. Electronic scanning is preferable for various aspects such as for high speed scanning, directivity and accuracy in the estimation of a defect position as hereinafter described. Further, in the case of electronic scanning, electronic linear scanning and electronic sector scanning are compared.

Figure 5:
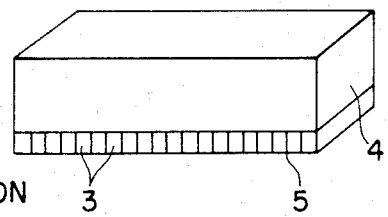
FIG. 5 is a schematic view of a phased array probe.

The principle of electronic scanning will be explained as follows:

Referring to FIG. 5, a phased array probe is composed of a large number of elements 3 aligned on a plane of a substrate 4 and coating 5 is applied to the surface of the elements 3. The shape of the ultrasonic beam irradiated from the probe is controlled by time control circuit. As shown in FIG. 6 (I) for example, if the delay time is equal for all of the elements the ultrasonic beam S forms a wave surface equivalent to that from a single transducer with a large width. If the delay time is set suitably, the beam S may be deflected as shown in FIG. 6 (IIa) or focussed as shown in FIG. 6 (IIb) or focused and deflected as shown in FIG. 6 (IIc) so as to form the beam profile as desired.

When this probe is scanned in an electronic scanning system, the favorable features of this electronic scanning (either linear scanning or sector scanning) which become apparent are:

(I) high-speed scanning

High-speed scanning is easy in comparison to mechanical scanning.

(II) sharp directivity

Since a large number of elements are simultaneously operated in a phased array probe the elements as a whole are equivalent to single transducer with a large width and have sharp directivity.

(III) dynamic focusing

In a phased array probe as described above, a delay time of a prescribed amount may be supplied to the sending and receiving wave signals, whereby the beam can be focused in a manner similar to a concave transducer or a transducer with a lens and the inspection can be performed at high resolution. Since the focal length in this state can be set freely, the accuracy of detecting a small defect and also the accuracy of the estimated position of the defect can be improved by focusing the beam to the inspection region of a specimen. FIG. 7 shows the relation between the ultrasonic beam diameter during the inspection of a square billet and the S/N ratio of $\phi$ 2 mm side cave for reference.

(IV) Since an ultrasonic beam can be scanned by a fixed probe, a wide inspection region is obtained using one probe.

A comparison of electronic linear scanning and electronic sector scanning using a phased array probe having the above features will now be described.

Figure 8:
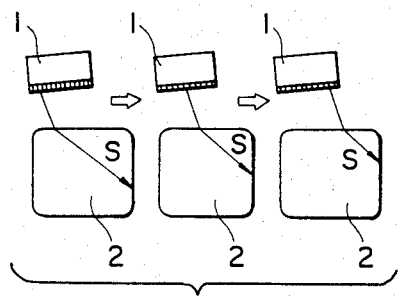
FIGS. 8 (a) (b) and (c) is a diagram illustrating the concept of electronic linear scanning of a square billet.
Figure 9:
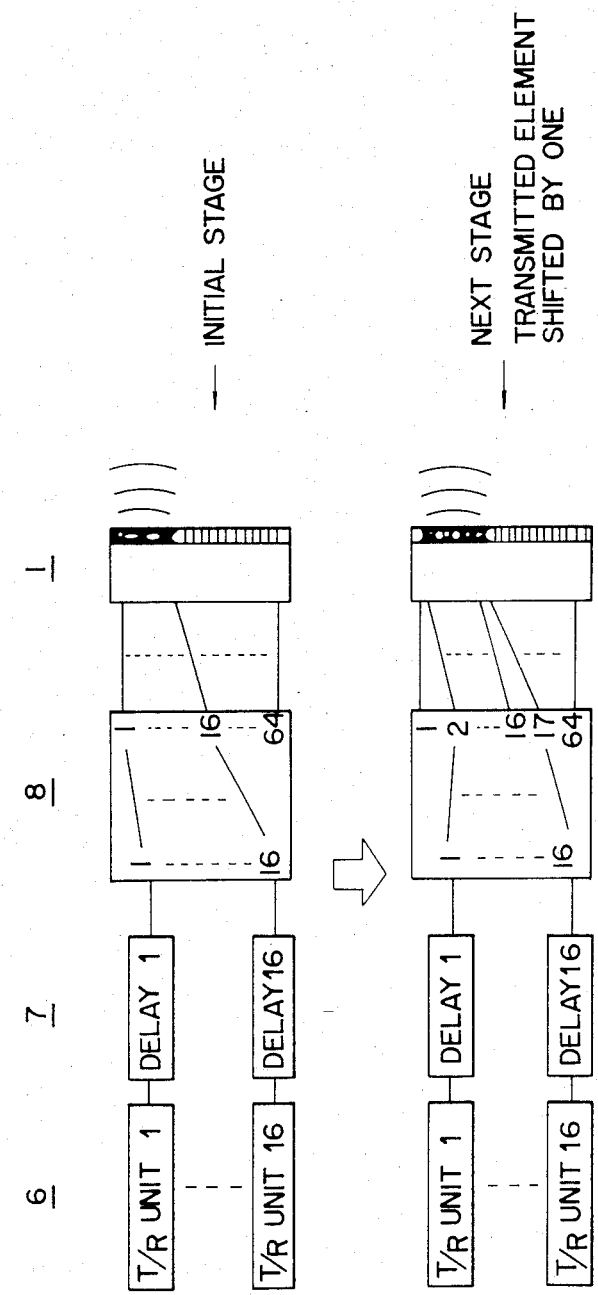
FIG. 9 is a diagram illustrating an example of a circuit arrangement for performing electronic linear scanning.

When electronic linear scanning is performed, a probe 1 is set to prescribed state and ultrasonic beam S is shifted in parallel as shown in FIGS. 8 (a) (b) and (c) and the inspection of a surface layer side of the adjacent lateral surface is performed. An example of the scanning circuit required for such process is shown in FIG. 9. A phased array probe composed of 64 elements in total has 16 elements as one set. The probe 1 and the transmitting/receiving device 6 are added to a delay circuit 7 as hereinbefore described and connected through a relay circuit 8. The ultrasonic beam is scanned when elements in the transmitting or receiving state are shifted in sequence by changeover switches.

Figure 10:
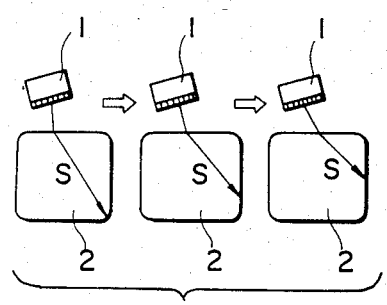
FIGS. 10 (a) (b) and (c) is a diagram illustrating the concept of electronic sector scanning of a square billet.
Figure 11:
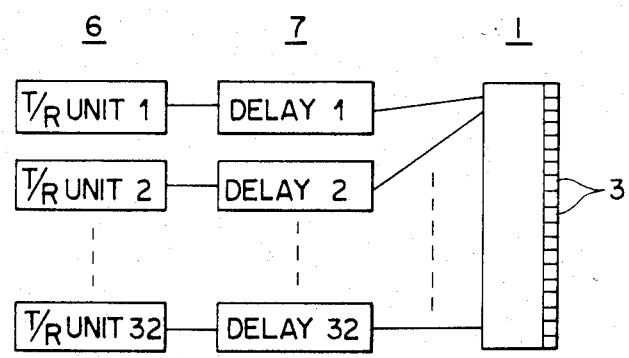
FIG. 11 is a diagram illustrating an example of a circuit arrangement for performing electronic sector scanning.

When electronic sector scanning is used, the probe 1 is set to a prescribed state in a similar manner. The ultrasonic beam S is deflected with respect to the incident surface as shown in FIGS. 10 (a) (b) and (c) and the inspection is performed at the lower half of adjacent lateral surface. An example of a scanning circuit required in such process is shown in FIG. 11. The probe 1 composed of 32 elements in total and the transmitting/receiving device 6 are connected in a one-to-one correspondence through the delay circuit 7. The setting of delay time according to the delay circuit 7 is varied in sequence whereby the inclination angle of the ultrasonic beam is varied and scanning is performed in beam deflection.

Moreover, the present invention is characterized by a combination of electronic sector scanning with electronic linear scanning based on hereinafter described principles.

Comparing electronic linear scanning with electronic sector scanning, the latter eliminates disadvantages of the former as hereinafter described. Therefore it can be said that the latter is more favorable.

(I) In electronic linear scanning, since elements in the transmitting or receiving state are shifted in a sequence the total number of elements increases thereby the probe becomes large.

(II) A large number of relays are required for the changeover but the life of the relays is short.

(III) Since elements in the transmitting or receiving state are shifted in sequence, the transmitting/receiving unit (T/R Unit) and each element are not in a one-to-one correspondence whereby any adjustment of the sensitivity variation is difficult.

(IV) Since the variation of the location of the incident point of the ultrasonic wave is large, the refraction angle varies depending on the surface unevenness of the square billet and the accuracy of the estimate of the defect position decreases.

Figure 12:
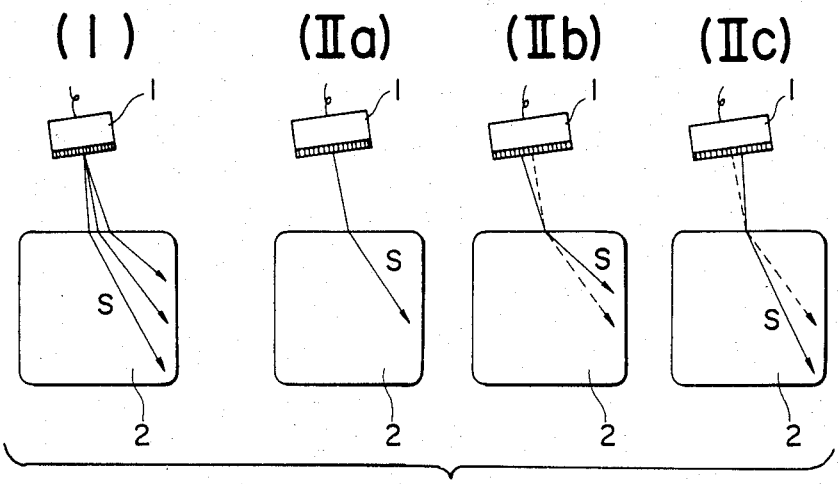
FIGS. 12 (I) (IIa) (IIb) and (IIc) is a diagram illustrating the comparison of electronic sector scanning with a combination of electronic sector scanning and linear scanning.

On the other hand, electronic sector scanning has the disadvantages that the incident point on the incident surface of the square billet 2 is shifted on account of the deflection of the ultrasonic beam S as shown in FIG. 12 (I).

In order to eliminate the above-mentioned disadvantages of electronic sector scanning, the present invention combines linear scanning with electronic sector scanning. As shown in FIGS. 12 (IIa) (IIb) and (IIc), the transmitting/receiving element is shifted corresponding to the beam inclination angle whereby the variation of the incident point location is suppressed to a minimum. The combined scanning method is affected by the unevenness of the incident surface no more than in electronic sector scanning and the accuracy of the estimate of the defect position can be improved.

The method of placing the probe for performing the combination of electronic sector scanning and electronic linear scanning having the above-mentioned features will now be explained.

Figure 13:
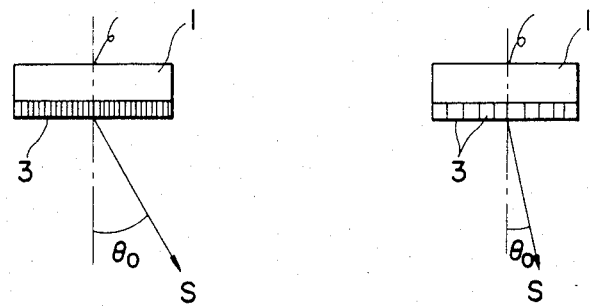
FIGS. 13a and 13b diagrams illustrating the relation between the element pitch of a phased array probe and the maximum beam inclination angle.

In a phased array probe the pitch d of the vibrator elements required to prevent the generation of a grating lobe when the maximum inclination angle of the ultrasonic beam S is assumed to be $\pm\theta_o$ is represented by $$d < \frac{\lambda}{1 + [\sin \theta_o]}$$

wherein $\lambda$ is the wave length in the ultrasonic transmission medium. In order to increase the inclination angle of ultrasonic beam S while $\lambda$ remains constant, the element pitch d must be decreased. (The relation between the element width and the maximum beam inclination angle $\theta_o$ is shown in FIGS. 13 (a) and (b).) Therefore the element width must be decreased.

In order to set a probe utilizating the above-mentioned features, the following two methods are proposed.

(1) One is a method in which a probe is disposed in a perpendicular plane with respect to the axial direction of a square billet, at a prescribed distance from the specimen surface and placed parallel to the incident plane. In this case, the width of each element of the probe is decreased and the number on a side is increased. The feature of this method is that both lateral surfaces adjacent to the incident surface can be inspected because the maximum beam inclination angle is large.

(2) The second is a method in which a probe is similarly disposed in a perpendicular plane with respect to the axial direction of square billet, at a prescribed distance from the specimen surface and set at an angle with respect to the incident surface with the incident angle establishing the center of deflection of the sector scanning. A feature of this method is that the absolute value of the beam inclination angle is small and therefore the maximum delay time may be decreased. The small absolute value of the beam inclination angle also permits a large width of each element of the probe.

Figure 14:
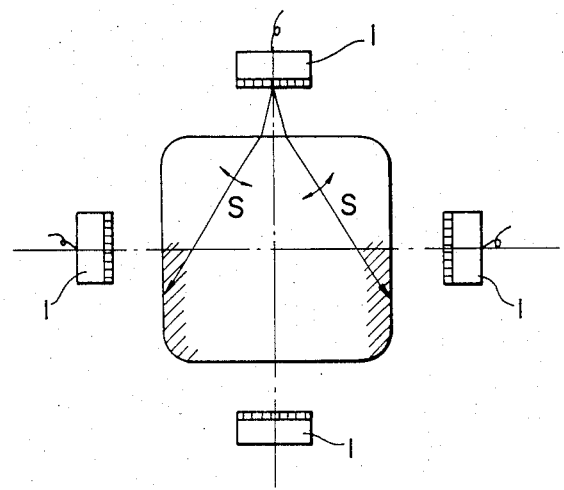
FIG. 14 is a diagram illustrating the application of one arrangement of probes to a square billet.
Figure 15:
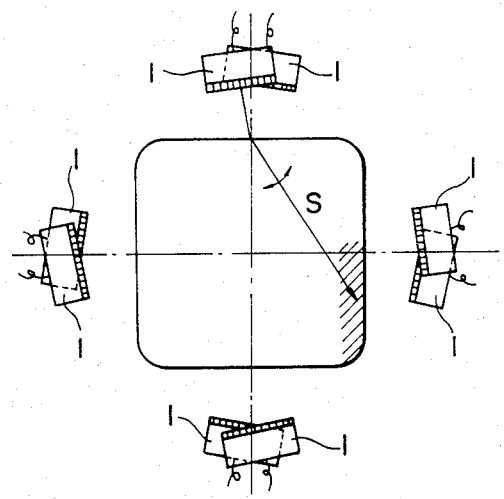
FIG. 15 is a diagram illustrating the application of another arrangement of probes to a square billet.

FIG. 14 and FIG. 15 show examples of arrangements of the probes 1 to the square billet 2. In the example of FIG. 14, one probe 1 is arranged in parallel to each surface of the square billet 2. That is, one probe 1 inspects the lower half of both lateral surfaces adjacent to the incident surface in the square billet 2 as seen in the figure. Thus four probes 1 can inspect the whole surface layer of the square billet 2. In another example shown in FIG. 15, two probes 1 are arranged at a prescribed angle to each surface of the square billet 2. That is, one probe 1 inspects the lower half of one lateral surface adjacent to the incident surface in the square billet 2 as shown in the figure. Thus eight probes 1 insepect the whole surface layer of the square billet 2. In either arrangement, a high-speed inspection is possible throughout the whole surface of the square billet in an on-line system.

The process of discriminating subsurface defects in a square billet will now be described. According to the angle beam inspection method of the present invention using a combination of electronic sector scanning and linear scanning, a square billet as a specimen can be inspected throughout its whole surface for detecting internal defects including subsurface defects at high speed and with accuracy. If the surface layer of the square billet is inspected, not only subsurface defects but also surface cracks are detected whereby the inspection results include information regarding the detection of surface defects. However, a surface crack can be removed by chipping or grinding the work in the steel machining process and therefore there is no problem in the secondary conditioning of the product. Accordingly, it is necessary only to detect internal defects (including subsurface defects) without detecting surface cracks.

In order to detect internal defects, the results of a surface defect inspection may be substracted from the results of an ultrasonic angle beam inspection of the inside of a square billet as described above. Various methods of surface defect inspection togther with their detecting capabilities are shown in following table.

TABLE

| sort of defect inspection method | internal defect | subsurface defect | surface defect | | |
|---|---|---|---|---|---|
| | | | crack | scab | scratch |
| Ultrasonic inspection by angle beam | O | O | O | O | O |
| surface wave inspection | X | X | O | O | O |
| magnetic powder inspection | X | X | O | Δ | X |

Since the detection capabilities for surface defects is different for the various methods of surface defect inspection, the detecting characteristics of internal defects depends on which method of surface defect inspection is combined with the internal defect inspection.

Figure 16:
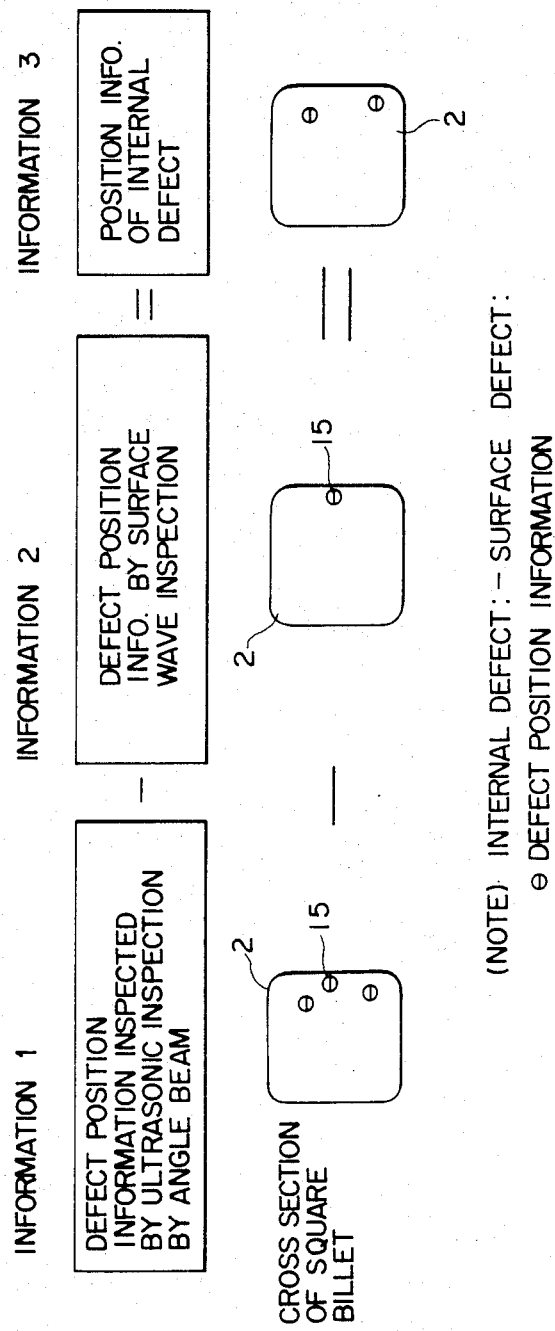
FIG. 16 is a diagram illustrating an information processing and detection pattern for discriminating internal defects including subsurface defects.

An information processing method for discriminating subsurface defects is effected basically by the subtration of information 2 from information 1 as shown in FIG. 16. However, since the ultrasonic angle beam inspection includes many factors which decrease the accuracy of the estimate of the defect position, information 1 is inferior in reliability to defect position information 2 based on surface defect inspection. The error range of the defect position estimate in information 1 is large. A simple subtraction therefore may cause errors.

Figure 17:
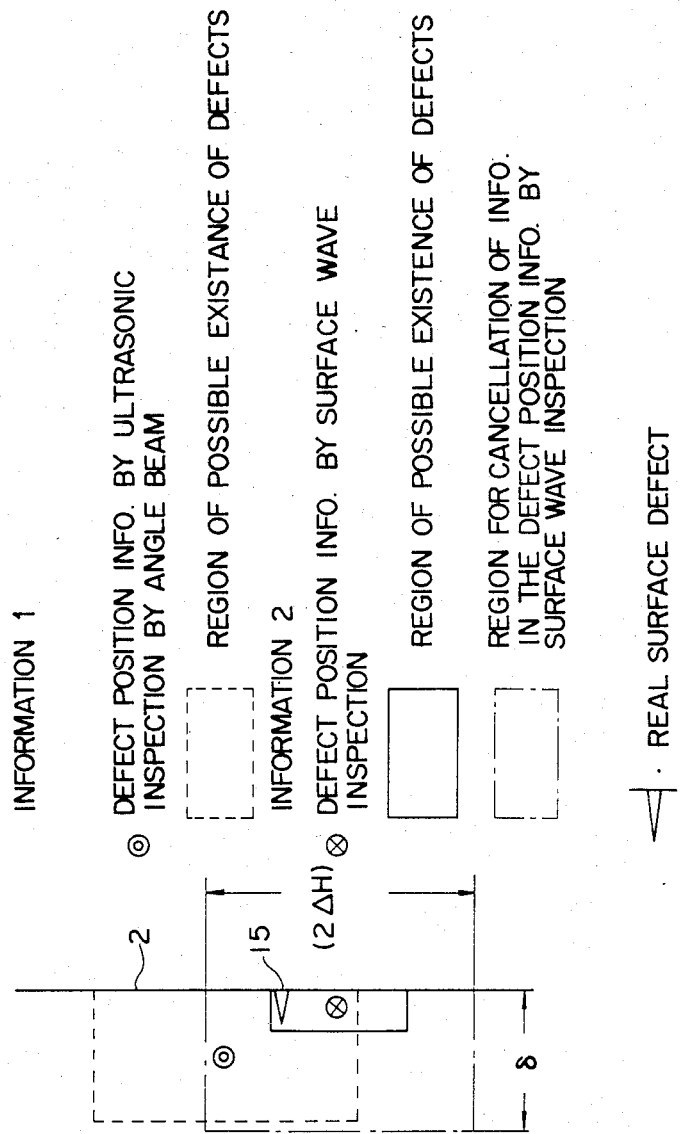
FIG. 17 is a diagram illustrating the principle of discrimination processing.

Referring to FIG. 17, surface defect 15 really exists. Information 1 indicates that the defect position detected using an ultrasonic angle beam inspection is at the position of the mark⊙ and, further, information 2 indicates that the surface defect position detected using another surface defect inspection device is at the position of the mark ⊗. If such information is processed without correction, it will be determined that each defect exists separately and information 1 showing the existence of a subsurface defect will remain. That is, although only a surface defect 15 really exists, it will also be shown as a subsurface defect.

In order to eliminate such incorrect detections of surface defects as subsurface defects, information 2 may be supplied with an extended region so that any information 1 entered within that region is cancelled. The extent of the region supplied to information 2 is determined according to the accurracy of information 1, and the accuracy is affected significantly by the ultrasonic diameter (Small diameter i.e. focussed state is preferable) and shape of incident surface. (Since unevenness of the incident surface varies in the apparent refraction angle, it is referable that the incident point varies little and the incident surface is flat).

The region determined for information 2 is shown by the dash-and-dot line in FIG. 17 and must be greater than the error region of the defect position estimate of information 1 (shown by a broken line). If information 1 is within a range of width $\pm \Delta$ H in the square billet width direction with respect to the surface defect estimated position (mark $\otimes$) of information 2, then the whole inspection region ($\delta$) in the depth direction, i.e. within the region shown by a dash-and-dot line, of information 1 is cancelled. Thus, a decisiion is made that information 1 is a surface defect by supplying an enlarged region to information 2.

The cancellation of information from the inspection by angle beam at width $\pm \Delta$ H in the width direction of the square billet 2 can cause incorrect decisions that the detection of a real subsurface defect in the region is deemed not to be subsurface defect. In order to decrease the probability of such a mistake the width of $\pm \Delta$ H must be decreased. In other words, the introduction of a scanning system having a high accuracy in estimating the defect position is preferable in an angle beam inspection.

Linear scanning is significantly affected by shape irregularity of a specimen and therefore is inferior to sector sanning in the accuracy of the defect position estimation. Accordingly, sector scanning is preferable. Of course, a combination of sector scanning and linear scanning is best since the position variation of the incident point is reduced to a minimum.

In order to improve the accuracy of the defect position estimation by a combination of sector scanning and linear scanning, the following two methods may be used concurrently.

One method is that the ultrasonic wave enters at a surface center portion which seems the least affected by the unevenness of the incident surface. In this arrangement, even if unevenness exists at the surface of the square billet 2, the surface center portion acts approximately like a flat surface as shown in FIGS. 18 (a) and (b).

Another method is that the echo from a corner portion is detected and the incident angle corresponding to the maximum value of the echo is determined so as to correct the apparent variation of the refraction angle ($S_o - S$) caused by the inclination of the incident surface as shown in FIG. 19. The inclination of the incident surface is estimated from the value of the incident angle, and the incident angle may be corrected so that the beam falls within the required inspection region.

Various surface defect apparatus for detecting surface defects 15 will be described.

Surface defect inspection methods include the magnetic particle inspection method, the eddy-current inspection method, the surface wave inspection method and the optical inspection method, and apparatus suitable for the respective methods are known. The detecting capability of these apparatuses is different depending on the various surface defect inspection methods and the kinds of defects.

The detecting capability of various inspection methods in regard to various sorts of surface defects as shown in FIG. 20 is set forth in the table described above. In FIG. 20, numeral $15_a$ designates a crack, numeral $15_b$ a scab and numeral $15_c$ a scratch.

As seen from the table, every sort of surface defect detected using angle beam inspection can be detected using surface wave inspection, but these defects except for crack $15_a$ cannot be detected using magnetic particle inspection. In surface wave inspection, however, when one surface defect is found, the propagation of sound waves farther from the defect point is significantly reduced. Therefore surface wave inspection may fail to find surface defects when there exist a number of these surface defects.

As above described, various surface defect inspection methods have both merits and demerits. The discriminating property of surface defects 15 and subsurface defects is dependent on a combination of various methods with angle beam inspection.

Information processing for discriminating surface layer defects from surface defects when using phased array apparatus for angle beam inspection and using surface wave inspection apparatus and magnetic particle inspection apparatus for surface defect inspection, will be described.

First, a data processing method for angle beam inspection will be explained.

Figure 21:
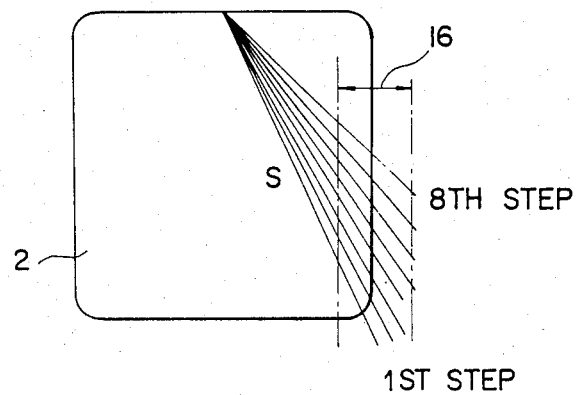
FIG. 21 is a diagram illustrating a combination of electronic sector scanning and linear scanning.

Referring to FIG. 21, the inspection region of a phased array apparatus is scanned by a combination of sector scanning and linear scanning in eight steps with the lower corner as reference point. If there is an echo beyond an echo threshold level which is previously set for each step in the inspection region, the step No. corresponding to the maximum echo, the echo height, the detecting time and the axial position of the square billet 2 are recorded as inspection data as shown in FIG. 22. The projection of the estimated position of the defect onto the square billet surface is estimated from the refraction angle and the detecting time. The estimated postion is divided by the pitch to obtain information as to the location in the width direction of the square billet. Data is collected when a defect continuity exists in the axial direction of the square billet 2, and information regarding defect No, defect starting point (axial direction), defect length (axial direction) and position in the width direction is determined.

In FIG. 21, the inspection gate 16 in the inspection region has a sufficient length to assure inspection of the surface even when the passage varies due to deformation of the specimen 2. In the corner portion, however, the region of the inspection gate is limited so as not to detect corner echo.

FIG. 22 (a) shows a cross-section of the square billet 2. Numeral 17 designates the position of a detected defect, and numeral 18 indicates the projection estimation position of the defect. FIG. 22 (b) shows the projection surface matrix of the square billet 2. $P_1$ designates the pitch of scanning step, and $P_2$ indicates the inspection pitch in the axial direction of the square billet. Information 18 of the projection estimation position of the defect is collected on the matrix. If the information 18 does not continue in two or more rows in the axial direction of the square billet, it is considered noise 19 and not made part of the defect information. If the information 18 continues twice or more, it is processed as defect information 20. That is, the detected defect 17 is made information, shown as enclosed by thick frame in FIG. 22 (b) and having starting point 21 and length (l).

Although the above description was made in regard to a combination of sector scanning and linear scanning by an electronic scanning type inspection apparatus, similar processing can be effected by linear scanning or sector scanning. Although the inspection region is inspected in eight steps, for example, it is clear that as the number of steps is increased, the inspection is performed more closely and the division of the width of the billet by the pitch during projection onto the surface can be performed more finely whereby the discriminating property can be improved.

A data processing method for surface defect inspections will be described.

Figure 23:
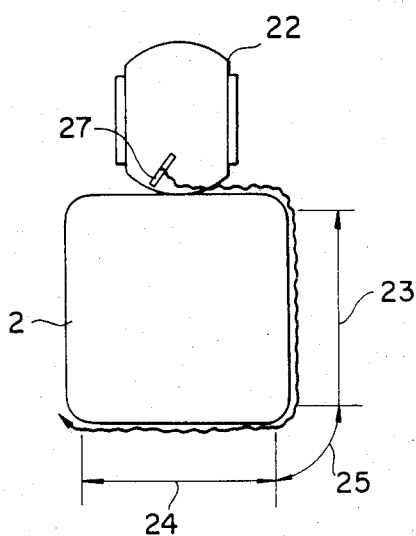
FIG. 23 is a view illustrating the inspection regions of a wheel type probe.

As shown in FIG. 23, a wheel type probe is used for surface wave inspection. The inspection regions in this case are the adjacent lateral surface 23, the opposed surface 24 to the surface contacted by the probe and corner portion 25. The inspection region is divided into three parts, i.e. the surfaces and the corner portion. The echo height, the detecting time and the axial position of the square billet are recorded as the inspection data in regard to a maximum of three echos which exceed a threshold value in part 23 and part 24 and in regard to the maximum echo exceeding the threshold value in corner gate portion 25. The estimated position of the defect in the axial direction of the square billet is estimated from detecting the time in a similar manner to the collection of data in inspection by angle beam, and the estimated position is converted into width position information by dividing it by the definite pitch. In view of the continuity of axial direction of the square billet, information regarding the defect No., the defect starting point (axial direction), the defect length (axial direction) and the position in the width direction is determined.

Regarding the inspection data obtained using a magnetic particle inspection apparatus, the information format is similar to that used in the collection of information by angle beam inspection and surface wave inspection.

Figure 24:
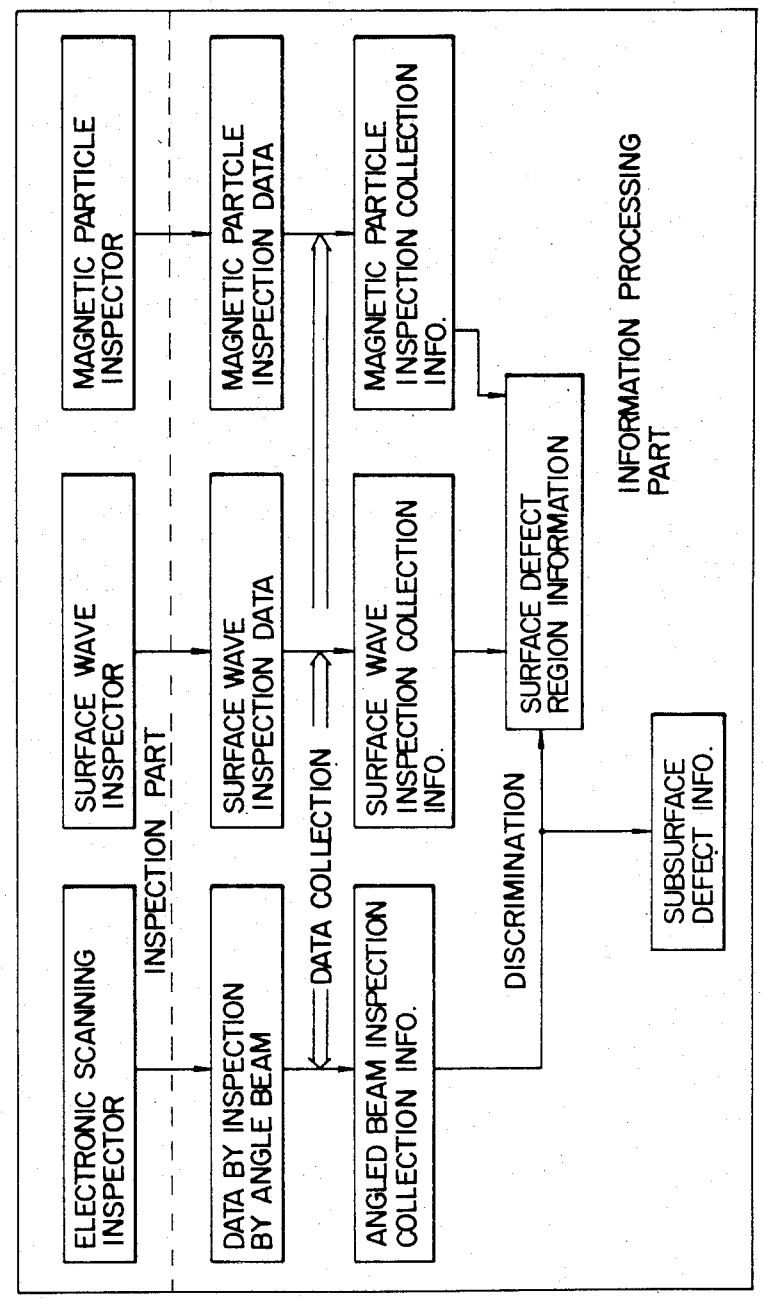
FIG. 24 is a flow chart of discrimination processing.

In order to discriminate surface defect information from information obtained by angle beam inspection, the information associated with each surface defect is supplied with an enlarged region which is used as the surface defect region information and subtracted from information collected by the angle beam inspection as already described. A block diagram of this process is shown in FIG. 24.

The suface defect region information includes position information about the position of the surface defect in the width direction, information collected from surface wave inspection or magnetic particle inspection or both, expanded for several blocks in the width direction of the square billet the defect starting point and the defect length in the region extending for several tens of mm.

Figure 25:
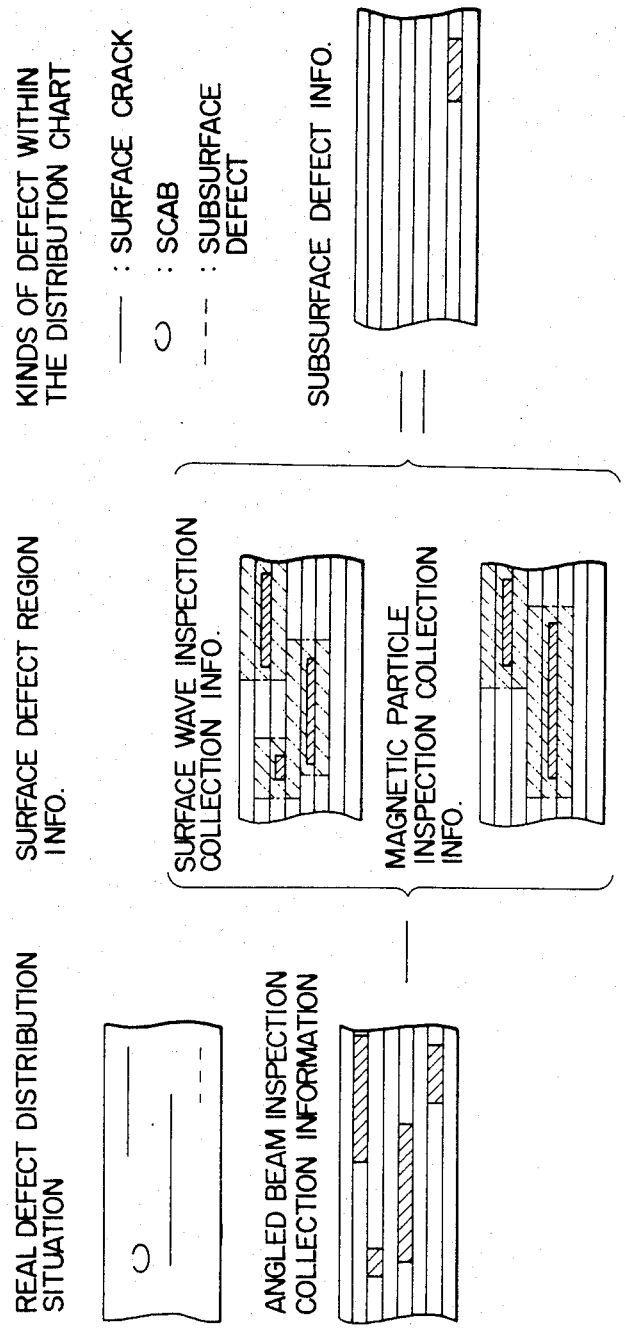
FIG. 25 is a diagram illustrating the concept of discrimination processing.

FIG. 25 shows the concept of the discriminating processing in the invention. It is understood from the figure that an incorrect detection in treating a surface defect as a subsurface defect can be prevented by a combination of surface wave inspection and magnetic particle inspection.

Figure 26:
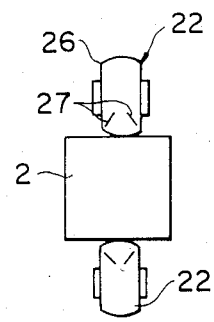
FIG. 26 is a view illustrating the arrangement of wheel type probes.

A probe arrangement for an angle beam inspection throughout whole surface was already described. The arrangement of a wheel type probe in an inspection throughout the whole surface will now be described referring to FIG. 26. Two probes 27 are contained in a wheel type probe 26, and two wheel type probes 22 are on opposite sides of the specimen. Of course, the specimen is moved in the axial direction.

In the above-mentioned embodiment of the invention, the phased array apparatus, surface wave inspection apparatus and magnetic particle inspection apparatus are combined, so that a surface defect can be discriminated from subsurface defect. Moreover, surface defects can be detected very accurately compared to surface defect inspection alone. Particularly in magnetic particle inspection, a low detecting capability of defects in a corner portion can be covered by inspection information in a corner portion gate from the surface wave inspection.

Figure 27:
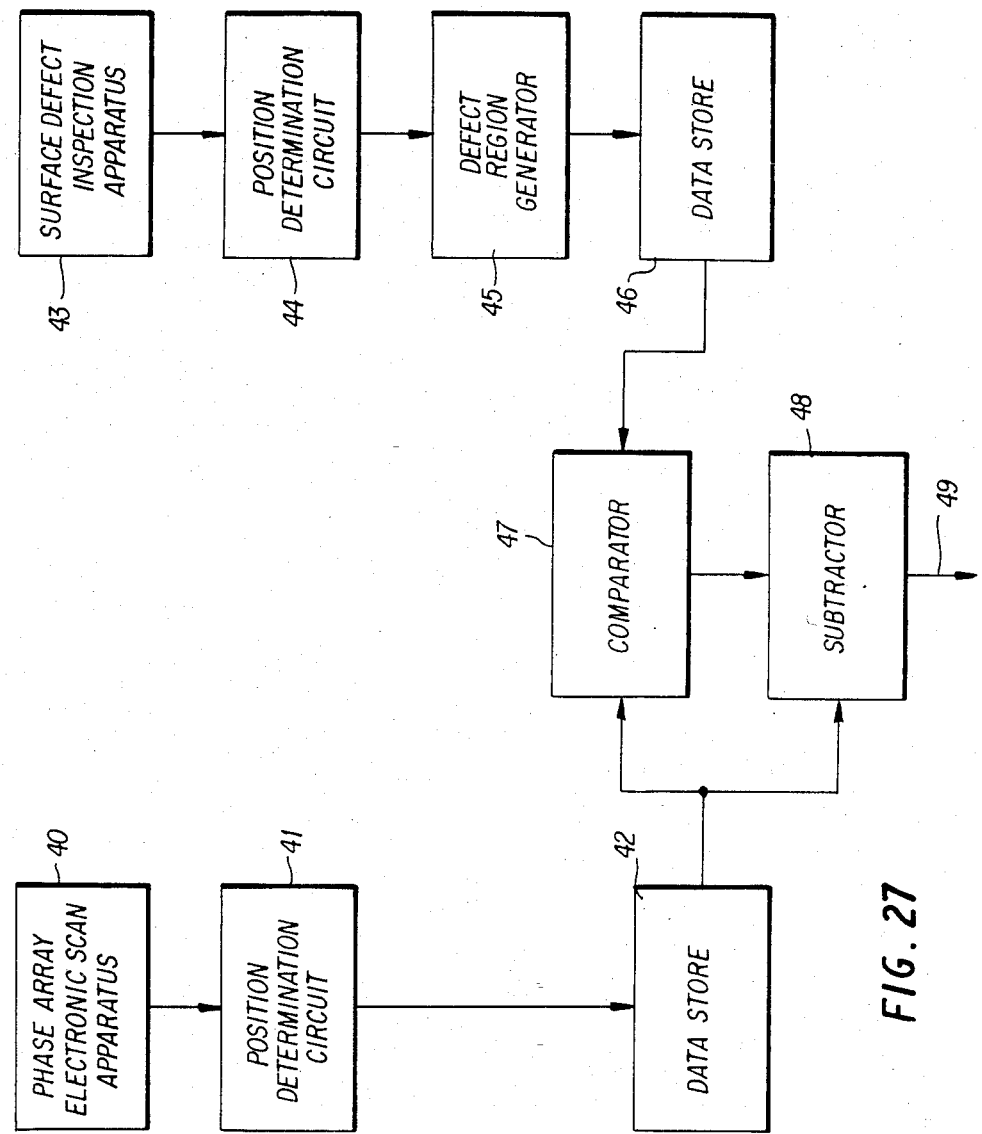
FIG. 27 is a block diagram of an electronic circuit for performing the method of the present invention.

FIG. 27 is a block diagram showing the arrangement of the apparatus for performing this method. The phase array, 40, electronically scans the billet to be examined. Both internal and surface defects in the billet are detected by this apparatus. The output of the scan is forwarded to a circuit for detecting the position of each defect in the position determination circuit 41. The location of each defect is then stored in data store 42. The billet is also inspected by way of surface defect inspection apparatus 43, which may be either a surface wave inspection device or a magnetic particle inspection device. This apparatus detects only surface defects. The position determination circuit 44 acts in a similar manner to circuit 41 in determining the position of each surface defect. The results of this determination are forwarded to a defect region generator 45 for generating a region around each defect location. This is necessary since there is a certain amount of error involved with the ultrasonic scan procedure. These regions are stored in data store 46. At the appropriate time, data from data stores 42 and 46 are forwarded to comparator 47 to determine when a defect located by the electronic scanning apparatus occurs at the same point as a defect detected by the surface defect inspection apparatus. When this occurs, a surface defect is involved. The comparator sends an indication of this condition to a subtractor 48 which removes information concerning this defect from the position data stored in data store 42 to produce the resultant output 49 which includes only the information concerning internal defects.

The present invention is not limited to the above-mentioned embodiments. A specimen may also be a rod, and in this case an annular array type probe such as set forth in Japanese patent application No. 58-3198 can be used to perform the inspection of the surface layer and surface simultaneously so as to discrimate defects.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of detecting subsurface defects in a specimen by ultrasonic inspection, comprising the steps of:
   detecting both internal and surface defects by an angle beam inspection on the surface layer of said specimen using a phased array probe;
   determining the projection on the surface of the estimated position of a said defect located by said angle beam inspection utilizing the positional relation of said probe and said specimen, the incident angle of the ultrasonic beam, and the defect echo detecting time;
   detecting surface defects only using a surface defect inspection apparatus;
   determining a defect region for each surface defect detected by said surface defect inspection apparatus;
   comparing said estimated defect position information with said defect regions to determine surface defect position information; and
   detecting only subsurface defects by subtracting said surface defect region information from said estimated defect position information.

2. A method of ultrasonic inspection according to claim 1 wherein said inspection is by linear scanning.

3. A method of ultrasonic inspection according to claim 1 wherein said inspection is by sector scanning.

4. A method of ultrasonic inspection according to claim 1 wherein said inspection is by a combination of linear scanning and sector scanning.

* * * * *